(12) United States Patent
Kamen et al.

(10) Patent No.: US 10,368,850 B2
(45) Date of Patent: Aug. 6, 2019

(54) SYSTEM AND METHOD FOR REAL-TIME ULTRASOUND GUIDED PROSTATE NEEDLE BIOPSIES USING A COMPLIANT ROBOTIC ARM

(71) Applicant: Siemens Medical Solutions USA, Inc., Malvern, PA (US)

(72) Inventors: Ali Kamen, Skillman, NJ (US); John Benson, Issaquah, WA (US); Richard Chiao, Cupertino, CA (US); Dorin Comaniciu, Princeton Junction, NJ (US); Ankur Kapoor, Plainsboro, NJ (US); Yuehaw Khoo, Princeton, NJ (US); Andrzej Milkowski, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 287 days.

(21) Appl. No.: 14/743,123

(22) Filed: Jun. 18, 2015

(65) Prior Publication Data

US 2015/0366546 A1    Dec. 24, 2015

Related U.S. Application Data

(60) Provisional application No. 62/013,850, filed on Jun. 18, 2014.

(51) Int. Cl.
*A61B 10/04* (2006.01)
*A61B 8/00* (2006.01)
(Continued)

(52) U.S. Cl.
CPC .............. *A61B 10/04* (2013.01); *A61B 5/055* (2013.01); *A61B 5/066* (2013.01); *A61B 5/067* (2013.01);
(Continued)

(58) Field of Classification Search
CPC .. A61B 5/00; A61B 8/00; A61B 10/00; A61B 34/00; A61B 2017/00;
(Continued)

(56) References Cited

U.S. PATENT DOCUMENTS

| | | | | |
|---|---|---|---|---|
| 4,860,215 A | * | 8/1989 | Seraji | B25J 9/163 700/260 |
| 8,016,777 B1 | * | 9/2011 | Egorov | A61B 5/0053 600/587 |

(Continued)

OTHER PUBLICATIONS

Ihnatsenka, Barys, and André Pierre Boezaart. "Ultrasound: Basic understanding and learning the language." International journal of shoulder surgery 4.3 (2010): 55.*

(Continued)

*Primary Examiner* — Luther Behringer
*Assistant Examiner* — Sean D Mattson

(57) ABSTRACT

Systems and methods are provided for utilizing an MRI image and real-time an ultrasound images to guide and/or restrict the movement of an ultrasound probe in position for collecting a biopsy core. A real-time ultrasound image is acquired and fused with pre-operative imaging modalities, such as an MRI image, to provide a three-dimensional model of the prostate. A multi-link robotic arm is provided with an end-effector and an ultrasound probe mounted thereto. Sensor information is used to track the ultrasound probe position with respect to the 3D model. The robotic arm allows for the implementation of a virtual remote center of motion (VRCM) about the transrectal probe tip, an adjustable compliant mode for the physician triggered movement of probe, a restrictive trajectory of joints of the robotic arm and active locking for stationary imaging of the prostate.

13 Claims, 3 Drawing Sheets

(51) Int. Cl.

| | | |
|---|---|---|
| *A61B 10/02* | (2006.01) | |
| *A61B 8/08* | (2006.01) | |
| *A61B 8/12* | (2006.01) | |
| *A61B 5/055* | (2006.01) | |
| *A61B 34/30* | (2016.01) | |
| *A61B 5/06* | (2006.01) | |
| *A61B 90/11* | (2016.01) | |
| *A61B 90/00* | (2016.01) | |
| *A61B 17/00* | (2006.01) | |

(52) U.S. Cl.
CPC .............. *A61B 8/12* (2013.01); *A61B 8/4218* (2013.01); *A61B 8/483* (2013.01); *A61B 8/5261* (2013.01); *A61B 10/0233* (2013.01); *A61B 34/30* (2016.02); *A61B 90/11* (2016.02); *A61B 8/429* (2013.01); *A61B 8/4405* (2013.01); *A61B 8/4444* (2013.01); *A61B 2010/045* (2013.01); *A61B 2017/00274* (2013.01); *A61B 2090/065* (2016.02); *A61B 2090/378* (2016.02)

(58) Field of Classification Search
CPC ..... A61B 2090/00; A61B 34/30; A61B 10/04; A61B 10/0233; A61B 90/11; A61B 5/055; A61B 5/066; A61B 5/067; A61B 8/12; A61B 8/4218; A61B 8/483; A61B 8/5261; A61B 8/429; A61B 8/4405; A61B 8/4444; A61B 2090/065; A61B 2090/378; A61B 2010/045; A61B 2017/00274
See application file for complete search history.

(56) References Cited

U.S. PATENT DOCUMENTS

| | | | | | |
|---|---|---|---|---|---|
| 2008/0021317 | A1* | 1/2008 | Sumanaweera | ...... | A61B 8/4218 600/437 |
| 2008/0186378 | A1* | 8/2008 | Shen | ............. | A61B 8/0833 348/65 |
| 2008/0306384 | A1* | 12/2008 | Boctor | .............. | A61B 8/08 600/443 |
| 2009/0005707 | A1* | 1/2009 | Sarvazyan | ........... | A61B 5/1077 600/587 |
| 2010/0286517 | A1* | 11/2010 | Kamen | ............ | A61B 10/0241 600/438 |
| 2010/0331690 | A1* | 12/2010 | Li | ............. | A61B 5/055 600/443 |
| 2012/0321165 | A1* | 12/2012 | Suda | .............. | G01S 7/5205 382/131 |
| 2013/0102891 | A1* | 4/2013 | Binnekamp | ........ | A61N 5/1007 600/424 |
| 2013/0102932 | A1* | 4/2013 | Cain | ............ | A61N 7/00 601/2 |
| 2014/0039314 | A1* | 2/2014 | Stoianovici | ........ | A61B 8/0841 600/439 |
| 2014/0276032 | A1* | 9/2014 | Majewski | ........... | A61B 6/0407 600/431 |
| 2014/0296876 | A1* | 10/2014 | Poquet | ............ | A61B 90/50 606/130 |
| 2015/0201910 | A1* | 7/2015 | Zhao | .............. | A61B 10/04 600/424 |
| 2015/0209599 | A1* | 7/2015 | Schlosser | ........... | A61N 5/1049 600/427 |
| 2016/0015363 | A1* | 1/2016 | Tahmasebi Maraghoosh | | ............ A61B 8/429 600/443 |

OTHER PUBLICATIONS

Karamalis, Athanasios, et al. "Ultrasound confidence maps using random walks." Medical image analysis 16.6 (2012): 1101-1112.*
De Schutter, Joris. "A study of active compliant motion control methods for rigid manipulators based on a generic scheme." Robotics and Automation. Proceedings. 1987 IEEE International Conference on. vol. 4. IEEE, 1987.*
Hung, Andrew J., et al. "Robotic transrectal ultrasonography during robot-assisted radical prostatectomy." European urology 62.2 (2012): 341-348. (Year: 2012).*
Hungr, Nikolai, et al. "A 3-D ultrasound robotic prostate brachytherapy system with prostate motion tracking." IEEE Transactions on Robotics 28.6 (2012): 1382-1397. (Year: 2012).*
Bax, Jeffrey, et al. "Mechanically assisted 3D ultrasound guided prostate biopsy system." Medical physics 35.12 (2008): 5397-5410. (Year: 2008).*

* cited by examiner

SYSTEM AND METHOD FOR REAL-TIME ULTRASOUND GUIDED PROSTATE NEEDLE BIOPSIES USING A COMPLIANT ROBOTIC ARM

CROSS-REFERENCE TO RELATED APPLICATIONS

The present patent document claims the benefit of U.S. Patent Application No. 62/013,850, filed on Jun. 18, 2014, which is hereby incorporated by reference.

BACKGROUND

It is common to diagnose prostate cancer using transrectal ultrasonography (TRUS) guided needle biopsy procedures. A TRUS guided needle biopsy is often prescribed as a result of an elevated prostate-specific antigen (PSA) level or upon detecting a palpable nodule during a digital rectal exam. Introduction of ultrasound (US) image-guided prostate biopsies substantially increases the accuracy of a prostate biopsy over performing a blind biopsy, thus TRUS guidance has become a universally accepted method for prostate biopsy. While TRUS guided prostate biopsies are a clinically accepted method, the procedures retain a low sensitivity of approximately 60% and positive predictive value of only approximately 25%. Consequently, repeat biopsies are often required. For example, in over 20% of the cancer studies, more than one biopsy session is required for a physician to reach a diagnosis decision.

Three-dimensional visualization applications, such as magnetic resonance imaging (MRI), can clearly depict the prostate gland and prostate substructures, including the central, transitional, and peripheral zones. For example, T2-weighted images can depict nodules in the peripheral zone. Localizing a tumor foci and the peripheral zone with MRI before a prostate biopsy may increase the overall cancer detection rate and the biopsy yield. Additionally, functional information acquired from various MRI techniques, such as diffusion weighted imaging (DWI), dynamic contrast-enhanced (DCE) imaging or chemical shift imaging (CSI), may be used to further characterize the prostatic tumor tissue. Using this functional information during the ultrasound guided biopsy may substantially improve the sensitivity of the biopsy procedure.

For example, endorectal MRI images and findings for suspected tumor foci may be used to manually guide the placement of needles during TRUS guided biopsy. By localizing biopsy to suspected tumor lesions and other targets identified on the endorectal MRI image, the physician may visually correlate the locations in the endorectal MRI image with ultrasound images during a subsequent TRUS guided biopsy, increasing the accuracy of the TRUS guided biopsy to approximately 67%, as demonstrated in a study of 33 patients. However, correlating locations using an MRI image requires a tedious visual inspection.

Robotic arms have been developed for handling ultrasound probes. For example, the robotic arms may alleviate physician fatigue during scanning procedures. In a robotic system, a physician's grasp and input to the ultrasound probe may be detected, such as by a 6-axis force sensor, and multiple detected parameters may be used for compliance control and self-weight compensation of the ultrasound probe as the probe is moved and adjusted by the physician.

SUMMARY

The present embodiments relate to real-time ultrasound guided prostate needle biopsies using a compliant robotic arm. By way of introduction, one or more of the present embodiments include systems and methods for utilizing an MRI image and real-time ultrasound images to guide and/or restrict the movement of an ultrasound probe in position for collecting a biopsy core. A real-time ultrasound image is acquired and fused with a pre-operative imaging modality, such as an MRI image, to provide a three-dimensional model of the prostate. A multi-link robotic arm is provided with an end-effector and an ultrasound probe mounted thereto. Sensor information is used to track the ultrasound probe position with respect to the 3D model. The robotic arm allows for the implementation of a virtual remote center of motion (VRCM) about the transrectal probe tip, an adjustable compliant mode for the physician triggered movement of probe, a restrictive trajectory of joints of the robotic arm and active locking for stationary imaging of the prostate.

In a first aspect, a method for ultrasound guided prostate needle biopsies using a compliant user-driven robotic arm is provided. A three-dimensional image of a prostate is received and a three-dimensional model of the prostate is generated using the three-dimensional image. Using the compliant user-driven robotic arm, an ultrasound probe is guided into a position for a three-dimensional ultrasound sweep of the prostate and the three-dimensional ultrasound sweep of the prostate is performed using the ultrasound probe in the position. The three-dimensional model of the prostate is updated using image data from the three-dimensional ultrasound sweep. Based on the updated three-dimensional model of the prostate, a three-dimensional location is identified in the prostate for collecting a biopsy core, where a location from the three-dimensional diagnostic image is mapped to corresponding location from the image data from the three-dimensional ultrasound sweep. The ultrasound probe is guided into a position to collect the biopsy core with the robotic arm by restricting the trajectory of the robotic arm based on the identified three-dimensional location in the prostate and displaying the identified location.

In a second aspect, a system for ultrasound guided prostate needle biopsies using a robotic arm is provided. A processor is configured to receive a three-dimensional image of a prostate, wherein the processor generates a three-dimensional model of the prostate based on the received image. A multi-link robotic arm includes a plurality of joints, an end-effector attached to one of the plurality of joints and an ultrasound probe attached to the end-effector. The ultrasound probe is operably connected to the processor in order to capture an ultrasound image, wherein the processor updates the three-dimensional model of the patient based on the captured ultrasound image. A position sensor is provided for at least one of the plurality of joints. The position sensor is operably connected to the processor to map the position of the ultrasound probe with the updated three-dimensional model. A force sensor is operably connected to the processor. The force sensor is configured to detect input forces to the end-effector. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the FIG. 1 illustrates an embodiment of a system for ultrasound guided prostate needle biopsies using a robotic arm.

DETAILED DESCRIPTION OF EXEMPLARY EMBODIMENTS

Figure 1:
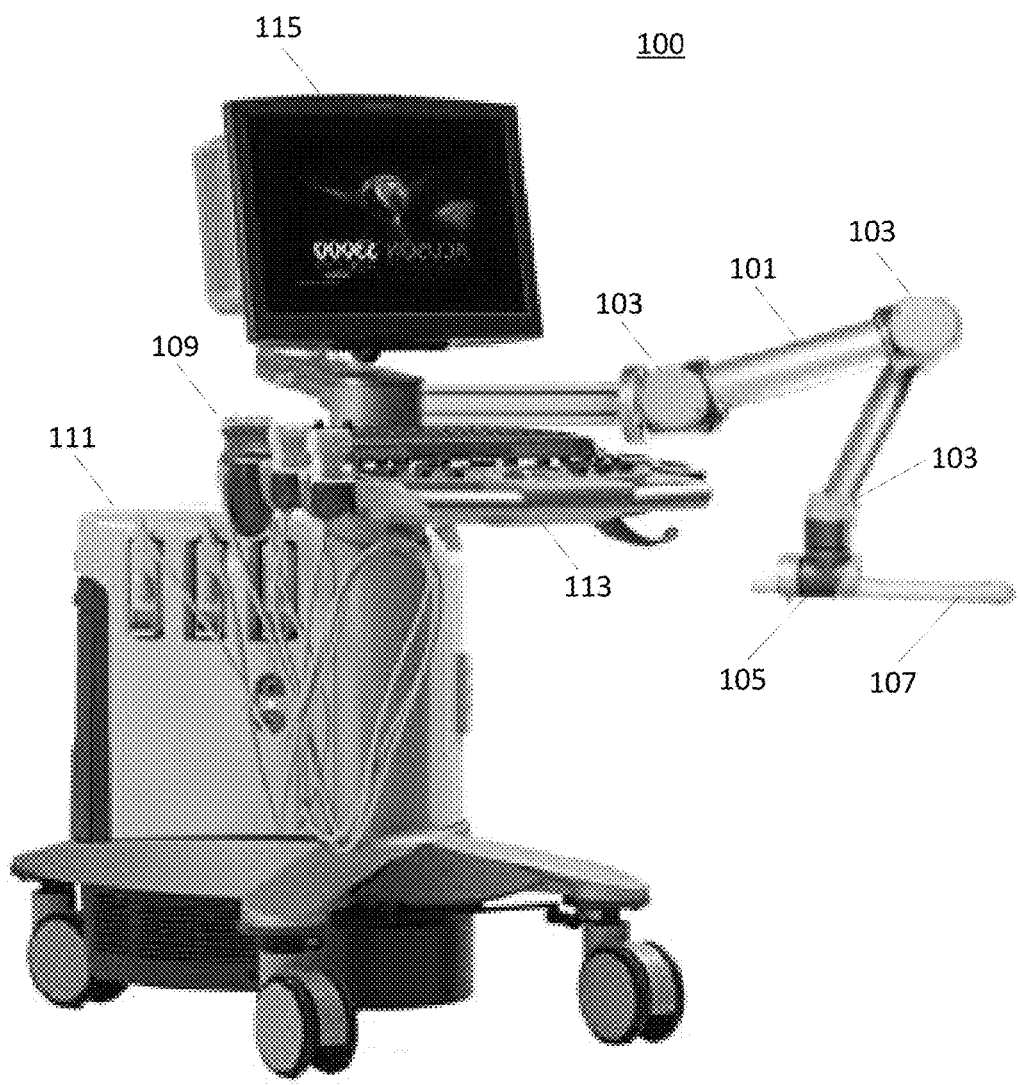

Current prostate biopsy procedures are performed systematically under ultrasound imaging guidance and often lack sensitivity in detecting malignant lesions. The present embodiments may increase the precision of prostate biopsy procedures used to detect cancer. To enhance sensitivity, a high quality three-dimensional scan, such as preoperative MRI data, is used during an ultrasound guided biopsy procedure. Information from the preoperative MRI data is used to determine an optimal placement of the biopsy needle cores in order to take accurate pathological samples, thus increasing the detection yields of the biopsy. For example, a real-time ultrasound image is fused with an MRI image to better target lesions within the prostate that are identified on the MRI image. An active compliant robotic arm is then used to track the position of the ultrasound probe attached to the end effector of the robotic arm. The user controls motion of the ultrasound probe by holding the probe handles, and the system detects the input force provided by the user measured by a decoder on the handle. The system also tracks the position of the ultrasound probe and the joints of the robotic arm in three-dimensions. The information received from of the ultrasound probe and the robotic arm allow for an active compliant and restrictive motion schemas for the robotic arm implemented within the control loop of the robot using the kinematics of the system. Further, a locking mechanism is provided that prevents all movement of the ultrasound probe and the robotic arm.

The disclosed embodiments may address challenges in fusion-based prostate biopsy by minimizing scanning variability, by addressing the effects of prostate deformation, by increasing ease of use and by increasing the precision in transferring MRI localized targets onto a real-time ultrasound sequence for guidance of the ultrasound probe. In doing so, a control loop allows the robotic arm to passively or actively manipulate the ultrasound probe held by the user using the real-time ultrasound images fused with pre-operative imaging modalities.

As such, one or more of the present embodiments provide an active compliant schema and restrictive motion, such as the trajectory of the robotic arm. For example, the trajectory of the robotic arm may be restricted by a virtual remote center of motion (VRCM or RCM) about the ultrasound probe tip. Further, automatic probe movement and scanning may be provided via the remote center of motion, or compliant movement that only allows the user to move the ultrasound probe in a specified manner (e.g., to maintain coupling pressure on the rectal wall). In another example, image analysis and feature tracking automatically adjusts the coupled pressure of the probe on the rectal wall and/or moves the probe to target an image-based location in the prostate. In another example, adjustable compliance of the robotic arm is provided. For example, compliance during any mode of operation, such as a "complaint" or "automatic" mode, restricts movement of the robotic arm based on a specific trajectory using a three-dimensional model of the prostate and/or a virtual remote center of motion of the probe.

FIG. 1 illustrates an embodiment of a system for ultrasound guided prostate needle biopsies using a robotic arm. The system 100 includes a multi-link robotic arm 101 and a workstation 109. The multi-link robotic arm 101 includes a plurality of joints 103, an end-effector 105 and an ultrasound probe 107. The robotic arm 101 is attached to an ultrasound machine, such as the workstation 109, or is freestanding, allowing the robotic arm 101 to be freely positioned by the user for better patient access. The end-effector 105 is attached to one of the plurality of joints 103, and the ultrasound probe 107 is attached to the end-effector. The multi-link robotic arm 101 also includes force sensors, position encoders, optical decoders and/or other sensors (not depicted in FIG. 1) provided at one or more of the plurality of joints 103. The workstation 109 includes a computer 111, a user interface 113 and a display 115. Additional, different, or fewer components may be provided.

The computer 111 is a computer platform having hardware such as one or more central processing units (CPU), a system memory, a random access memory (RAM), a graphics processor unit (GPU) and input/output (I/O) interface(s). Additional, different or fewer components may be provided. For example, the computer 111 may be implemented on one or more servers. In another example, workstation 109 includes a controller for controlling the robotic arm in addition to computer 111. In another example, the computer 111 is separate from or not part of the workstation 109.

The computer 111, or a processor therein, is configured to receive a three-dimensional representation of a prostate, such as preoperative or diagnostic MRI image or data. As used herein, the MRI image may be data from a scan prior to display, so may include a three-dimensional representation. Based on the three-dimensional image, the computer 111 is further configured to generate a three-dimensional model of the prostate. The three-dimensional model may utilize biomechanical properties of the prostate determined (i.e., Young's modulus and the Poisson's ratio) using nominal values reported from literature, or from personalized values extracted from elastography scans of the patient. Using the three-dimensional image and/or the generated three-dimensional model of the prostate, one or more biopsy cores are identified manually or automatically. The computer 111, or a processor therein, is further configured to receive one or more real-time ultrasound images captured by the ultrasound probe 107 operably connected therewith. Using the real-time ultrasound image, the computer 111, or a processor therein, is configured to generate an updated three-dimensional model. For example, the ultrasound probe 107 captures an ultrasound sweep of the prostate, and the three-dimensional model is updated to account for prostate deformation caused by the ultrasound probe. Further, feature locations identified using the preoperative MRI are updated in the updated three-dimensional model to account for the effects of the prostate deformation. In this example, one or more biopsy cores are identified using the updated three-dimensional model of the prostate.

The computer 111, or a processor therein, is configured to track the location and movement of the joints of the multi-line robotic arm 101, the end-effector 105 and/or the ultrasound probe 107. For example, a position sensor (not depicted in FIG. 1), such as an optical decoder or a position encoder, is attached to each of the plurality of joints 103 and is operably connected to the computer 111. The computer 111 is configured to map the position of the ultrasound probe, such as with respect to the updated three-dimensional model of the prostate. Using sensors or calibration, the position of the robotic arm 101 in the coordinate space of the MR or other preoperative system is known. Further, the computer 111, or a processor therein, is configured to receive user inputs at the end-effector 105 and/or the ultrasound probe 107. For example, a force sensor (not depicted in FIG. 1) is provided in close proximity to the joint 103 where the handle of the ultrasound probe 107 is attached to the end effector 105. In another example, the force sensor is attached to the handle of the ultrasound probe.

As discussed above, the position encoders at the joints 103 detect the kinematics of the robotic arm, allowing for real-time sensing of the ultrasound probe 107 location at all times during the procedure. An ultrasound calibration process is performed, with or without a phantom, to determine a transformation used to map ultrasound image points to a fixed coordinate system based on the location of the joints 103 of the robotic arm and the ultrasound probe 107 location. The real-time sensing of the joint 103 and the ultrasound probe 107 locations facilitate active or passive control over the robotic arm 101, and ultimately, the ultrasound probe 107. For example, the end-effector 105 or the ultrasound probe 107 includes a handle allowing the user to freely move the probe as required within the space allowable by the robotic arm's kinematics.

The robotic arm 101 is configured, via the computer 111, to operate in a plurality of operating modes to control the movement of the joints 103 and the ultrasound probe 107. For example, the robotic arm 101 operates in freestyle mode, active compliant mode, locking mode, RCM mode, automatic mode or a combination thereof. In freestyle mode, motion of the robotic arm is triggered by a user input and the motion is only limited by the structure of the joints (e.g., the mechanical design of the robotic arm).

In active compliant mode, motion of the robotic arm is triggered by a user input sensed by the force sensor and the robotic arm facilitates "weightless" movement of the end-effector. Further, the active compliant mode facilitates constraints on movement, such as restricting movement of the robotic arm to a specific trajectory or with respect to a particular location, such as a trajectory to perform a task or to avoid collision with another object in the room. For example, the control loop for the robotic arm senses a user input and assists the user in moving the robotic arm in the direction of the input (e.g., passively guiding movement of the robotic arm). As soon as the user input ceases, the robotic arm maintains its current position until another user input initiated.

In a locking mode, the joints 103 of the robotic arm 101 actively maintain their positions (i.e., restrict all motion of the robotic arm). In an example, the locking mode resists motion up to a certain threshold of exerted force on the end-effector 105, the handle of the ultrasound probe 107 and/or the joints 103.

In an RCM mode, motion of the robotic arm is restricted to movement about a fixed point, such as the distal end of the ultrasound probe. For example, the user manually performs a three-dimensional ultrasound sweep of a prostate by moving the ultrasound probe about a fixed point. In this example, the robotic arm restricts movement of the tip of the ultrasound probe, by keeping the tip of the probe in a fixed location, and allows the user to rotate the ultrasound probe about the tip to perform the ultrasound sweep. Thus, the robotic arm is passively guides the ultrasound probe by restricting the user's ability to manipulate the probe about the fixed location.

In an automatic mode, the ultrasound probe is moved automatically by the robotic arm. For example, the robotic arm automatically performs a three-dimensional ultrasound sweep of a prostate by moving the ultrasound probe about a distal end of the probe while capturing ultrasound images (e.g., actively guiding movement the robotic arm via a remote center of motion). The computer 111 or other processor controls the movement without user input other than activation. In another example, the robotic arm automatically moves the ultrasound probe into position to collect a biopsy core. The robotic arm automatically moves the ultrasound probe based on the detected ultrasound probe location, the detected robotic arm joint locations, the three-dimensional model of the prostate, the preoperative three-dimensional scan and/or the capture ultrasound images.

Additional, different or fewer modes and/or constraints on movement may be provided. For example, additional constraints may be included in any of the above mentioned modes, such as to avoid self-collision, collision with ultrasound machine, patient discomfort, and other constraints related to the prostate biopsy procedures. In another example, the robotic arm is restricted based on analysis of captured ultrasound images. The modes are user selectable. For example, the locking mode is triggered by a push button. Alternatively, the modes are automatically selected based on a system state or a workflow.

Figure 2A:
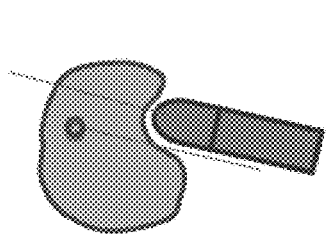
FIGS. 2A-C depict examples of prostate deformation caused by an ultrasound probe.
Figure 2B:
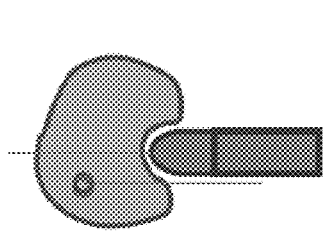
Figure 2C:
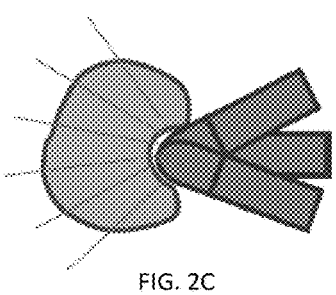

For example, in one or more modes discussed above, movement of the ultrasound probe is guided, constrained and/or restricted to maintain pressure on the prostate. For example, the robotic arm passively or actively guides the ultrasound probe to maintain consistent couple pressure of the ultrasound probe with the rectal wall in compliant mode, RCM mode and automatic mode. An ultrasound probe requires adequate coupling pressure to capture an ultrasound image, however, limited and uniform prostate deformation is also preferred and results in accurate ultrasound images. For example, FIGS. 2A-C depict examples of prostate deformation caused by an ultrasound probe. FIGS. 2A-B depict two positions of freehand sweep for biopsy cores (e.g., in a freestyle mode). As the ultrasound probe sweeps from the position in FIG. 2A to the position in 2B, the prostate is deformed differently, resulting in inconsistent ultrasound images of the prostate. The deformation caused by different positioning and/or pressure may cause the lesion or region to be biopsied to alter position with the prostate and/or relative to the probe. Conversely, FIG. 2C depicts an ultrasound sweep (e.g, in the complaint, RCM or automatic mode) minimizing prostate deformation variation between various probe positions. In addition to RCM mode, for example, coupling pressure and prostate deformation can be controlled by monitoring the captured ultrasound images (e.g., by monitoring de-correlation between consecutively captured ultrasound images, by monitoring a difference in a strain on prostate tissue between consecutively captured ultrasound images, by generating an image confidence map based on consecutively captured ultrasound images, or a combination thereof).

One or more of the above embodiments is provided by a control loop for the robotic arm. For example, the control loop can passively guide the ultrasound probe by receiving a user input and restricting the trajectory of the robotic arm based on constraints provided in the control loop. In another example, the robotic arm actively guides the ultrasound probe. In these example, image based constraint driven control of the robotic arm is provided by the control loop, such as by controlling the trajectory of the robotic arm. The image based constraints are derived by acquiring and fusing real-time ultrasound data with a pre-operative data modality, and mapping image-based constraints derived from the fused data to the coordinate space of the robotic arm. Constraint driven control in robotics provides constraints on the movement of the robotics, such as on the range of motion of a robotic arm. For example, constraint driven control can be used to apply constraints in order to perform specific tasks (e.g., task based constraints). For example, a remote center of motion is a task based constraint. One or more of the present embodiments implement image-based constraints in a control loop schema for a robotic arm.

The image-based constraints used in a control loop can be implemented using various implementations. The following equations and other mathematical representations are provided for illustrative purposes. Other implementations, equations and mathematical representations may be used.

For example, a constrained control schema for a robotic arm can be written as equation 1:

$$\Delta q = \min_{\Delta q} \sum g_i(\Delta q, \Delta x_i^d); \text{ s.t. } c_j(\Delta q, \Delta x_j) = 0 \quad \text{(Eq. 1)}$$

where $\Delta q$ is the incremental motion of the joints of the robotic arm (e.g., if the robotic arm has three joints, then $\Delta q$ is includes three vectors representing the incremental motion of the joints). The joint velocities of the robotic arm are linearized using the derivative $\Delta q/\Delta t = \dot{q}$, where $\dot{q}$ is joint velocities. Incremental Cartesian motion of the end-effector is linearized as $\Delta x_i$ and $\Delta x_j$, and functions $g_i$ and $c_j$ relate the incremental Cartesian motion of the end-effector to the incremental joint motion (e.g., relationships between end-effector motion and joint motion). Using the minimization of equation 1, a desired trajectory of the end-effector and joints of the robot is achieved taking into account the current end-effector and joint orientation and speed, and subject to one or more constraints placed on the movement. The same notation can be extended for an image based constrained control schema.

An image based Jacobian matrix can be applied to the constraint control schema to provide a linearized relationship between image features and the change in position of the end-effector and joints of the robotic arm. Using the image based Jacobian matrix, constraints are derived from image features in the image space, such as an RCM point or an identified biopsy location. Alternatively, an ultrasound probe based image Jacobian matrix can be applied to the constraint control schema to provide a linearized relationship between Cartesian features and the change in position of the end-effector and joints of the robotic arm. Using the ultrasound probe based Jacobian matrix, Cartesian based constraints from the Cartesian space are derived from features in the Cartesian space, such as the patient table and other equipment in the Cartesian space. Features in the Cartesian space are identified during calibration and are used for collision avoidance constraints. In an embodiment, constraints from the image space and the Cartesian space are applied in restricted space (i.e., areas where image based and/or Cartesian based feature constraints have been derived), restricting and/or guiding motion of the end-effector and joints of the robotic arm. In the unrestricted image and Cartesian space (e.g., areas where no constraints have been derived), movement of the robotic arm by the user is unconstrained (e.g., in a freestyle or complaint mode).

In an embodiment, applying image-based constraints, f is a set of observed features in the image space that are included in a vectorization of an entire image, and $\Delta f$ is the corresponding vector of rate of change of image features. An image Jacobian is used to perform a linear mapping from the tangent space of $x_k$ (e.g., the Cartesian position of the end-effector, or any other arbitrary coordinate frame attached to the robot) to the tangent space of the image features (e.g., $\Delta f$), written as equation 2:

$$\Delta f = J_I \Delta x_k \quad \text{(Eq. 2)}$$

Applying the manipulator Jacobian to equation 2 provides the linearized relationship between Cartesian position of the $k^{th}$ coordinate frame to the rate of change of joints of the robotic arm, written as equations 3 and 4:

$$\Delta f = J_I J_k \Delta q \quad \text{(Eq. 3)}$$

$$\text{where, } \Delta x_k = J_k \Delta q \quad \text{(Eq. 4)}$$

Using the image Jacobian from equations 2-4, equation 1 is rewritten, as provided in equation 5:

$$\Delta q = \min_{\Delta q} |\Delta x_i^d - J_i \Delta q| + \sum_{j=1}^{N} |\Delta x_j^o - J_j \Delta q| + \alpha^t s_1 + \beta^t s_t \quad \text{Eq. 5)}$$

$$\text{s.t. } |\Delta x_k - J_I J_k \Delta q|_2 \le \varepsilon_t + s_1 \forall k = 1 \ldots M$$

$$|\Delta x_t - J_t \Delta q|_2 \le \varepsilon_t + s_t \forall t = 1 \ldots P$$

where $J_k$, $J_t$, $J_i$ and $J_j$ are manipulator Jacobians for frames k, t, i and j, respectively, where $J_I$ is the image Jacobian. $\Delta x_k$, $\Delta x_t$, $\Delta x_i$ and $\Delta x_j$ are the incremental Cartesian positions for frames k, t, i, and j, respectively. The superscripts d and o refer to the desired incremental position of the ultrasound probe or handle i and the objective to be met j, respectively. In equation 5, there are P task based constraints, M image based constraints and N objectives. The task based constraints (e.g., RCM), image based constraints (e.g., constraints based on the ultrasound image and/or the preoperative MRI image) and the objectives (e.g., constraints based on the mechanical limits of the robotic arm) are met in addition to facilitating the desired movement of the ultrasound probe. Slack variables $s_I$ and $s_t$ may be included to relax the constraints, wherein the degree of slackness is controlled by parameters $\alpha$ and $\beta$, respectively.

Previously, the aforementioned constraints were either expressed as linear or nonlinear constraints. For example, constraint linearization has been accomplished by approximating a non-linear feasible data set approximating a closed polygon with n-sides. Nonlinear constraints have been solved using feasible sequential quadratic programs that convert the nonlinear constraints into a series of iterative quadratic equations while ensuring that the solutions remain within the feasible set. In these approaches, a trade-off between speed (e.g., via linear constraint methods) and accuracy (e.g., non-linear constraints) was made.

Trade-offs between speed and accuracy may not be required where no constraint linearization is performed. In an embodiment, a second-order cone programming (SOCP) is solved directly. For example, an objective can be expressed as any convex form of L1, L2 or L2 norm squared. Because each convex form has the same minimum associated therewith, the convex forms can be substituted for one another. The SOCP can be solved by algorithms such as an embedded conic solver (ECOS), which uses interior point methods for SOCP. As a result, it may be possible to solve this problem in the rates required for robot control (e.g., typically in less than 10 milliseconds).

In one or more embodiments, one or more of the following illustrative constraints are provided for ultrasound guided prostate biopsy with a robotic arm. For example, constraints are implemented using equation 5 with the SOCP solved directly. Additional, different or fewer constraints may be proved. For example, one or more constraints may be implemented unrestricted (e.g., allowing the robotic arm to be moved freely), as a soft constraint (e.g., resisting motion of the robotic arm in a specified way) or a hard restraint (e.g., preventing all motion of the robotic arm in a specified way).

Compliant adjustment and locking of the robotic arm may be helpful to the user to assist accurate movement of the ultrasound probe and to limit fatigue associated with ultrasound procedures. In an embodiment, compliant adjustment and locking of the robotic arm is provided. For example, compliant control of the robotic arm is provided using impedance control (e.g, via the relationship between force and position) or admittance control (e.g., the inverse of impedance control) of the robotic arm. For example, using admittance control (or pseudo admittance control), a lower level controller may be used, such as a proportional-integral-derivative (PID) controller that can drive the robotic arm to set an orientation and/or velocity of the robotic arm. In this example, a sensor is attached to the handle of the ultrasound probe, such as a force senor or an optical encoder capable of generating a signal proportional to user input. Therefore, if τ is the 6D user input from this sensor (e.g., force and torque measurements in thee Cartesian coordinates), then the desired incremental position of the ultrasound probe can be mapped using equation 6:

$$\Delta x_i^d = K\tau \quad \text{(Eq. 6)}$$

where K is a 6×6 scaling matrix. In compliant mode, the robotic arm receives a user input via the sensor and assists the user in moving the robotic arm, such as allowing "weightless" motion in response to an input. Further, for a locking mode, τ or the scaling matrix K are set to zero upon triggering the locking mode (e.g., when the system receives no user inputs or the locking mode is initiated by the system and/or user).

Virtual remote center of motion (VRCM or RCM) is a useful constraint of a medical robot control, such as to limit inconsistent prostate deformation. In an embodiment, a RCM for the robotic arm is provided. For example, the system or user directly selects the RCM point based on an image feature. For instance, the user can select a feature in the ultrasound image, the MRI image and/or a three-dimensional model, such as the apex of a prostate in the ultrasound image. A Jacobian is then computed for the selected feature with respect to joints of the robotic arm to implement the RCM about the selected feature set as the constraint. Therefore, if $x_p$ is the 3D coordinates of the desired RCM point in image space, then the RCM constraint can be written as equation 7:

$$|x_p + \Delta x_p - J_p J_p \Delta q|_2 \le \epsilon_I \quad \text{(Eq. 7)}$$

Unlike earlier RCM approaches, it may not be required that the RCM point be known to the system in Cartesian coordinates with respect to the end-effector of the robot or the ultrasound probe. Further, as discussed above, solving conic problems with interior point methods allows equation 7 to be solved directly instead of solving a linearized form or a locally linear solution. This is important if the tolerance of the RCM is crucial, such as in prostate TRUS procedures. For example, if the ultrasound probe tip moves too far away from the RCM point varies prostate deformation, causing a potential error in the needle guidance.

Further, it may be desirable to swiftly acquire a three dimensional volume of the prostate by compounding 2D US images by performing an ultrasound sweep. It may also be desirable limit prostate deformation during ultrasound sweep acquisition. In one or more embodiments, the pressure or force applied to the rectal wall is controlled and kept uniform across an ultrasound sweep. For example, referring back to FIGS. 2A-C, prostate deformation in FIG. 2C is minimized throughout an ultrasound sweep and consistent between positions of the ultrasound probe when compared to FIGS. 2A-B. Traditionally in robotics, end-effector force is measured and controlled using a force or pressure sensor mounted on the end-effector or the attached tool. However, this solution may not be practical for TRUS procedures due to limitations in available acoustically translucent force sensors, sensor size and cost implications. In this embodiment, image constraints are used as a substitute for a force or pressure sensor. For example, image derived features can be used to determine the pressure or force applied to the rectal wall, such as image correlation, image strain correlation and/or using an image confidence map based on comparison or differences between data for sequential scans.

In an embodiment, the pressure or force applied to the rectal wall is controlled and kept uniform by measuring the angular displacement between two consecutive ultrasound images to determine image correlation. For example, when the angular displacement between two consecutive positions is small, then the captured image are highly correlative. Therefore, if the pressure or force applied to the rectal wall changes between consecutive images, then the consecutively captured images will not be as correlated. By monitoring changes in correlation (or de-correlation) between consecutively captured images, the position of the ultrasound probe can be adjusted during the ultrasound sweep to maintain consistent pressure on the rectal wall.

In another embodiment, the pressure or force applied to the rectal wall is controlled and kept uniform by measuring image strain. For example, strain images use ultrasound shear waves and/or acoustic radiation force imaging to provide an estimate of strain on the tissue. Correlation in image strain between two consecutively captured images should be similar (e.g., between images captured before and after a small change in probe position). Metrics, such as cosine similarity, mutual information or other information theory metrics independent of image magnitude, are used to determine correlation between strain images. By monitoring changes in correlation (or de-correlation) between consecutively captured images, the position of the ultrasound probe can be adjusted during the ultrasound sweep to maintain consistent pressure on the rectal wall.

In yet another embodiment, the pressure or force applied to the rectal wall is controlled and kept uniform using an image confidence map. For example, an image confidence map is a learning model based on a probability map that labels each pixel in the image with a value between zero and one (e.g., 0 to 1). The learning model is used to identify acoustic shadows in an ultrasound image and/or an impedance mismatch between the ultrasound image and scanned surface. For example, acoustic shadows at the far edge of the image (e.g., the edge opposite the ultrasound probe) indicate that contact pressure is insufficient. Thus, when acoustic shadows in a confidence probability map are indicative of insufficient applied pressure, the position of the ultrasound probe can be adjusted during the ultrasound sweep to maintain adequate pressure on the rectal wall.

In an embodiment, the pressure or force applied to the rectal wall is measured using image correlation, image strain correlation and/or using an image confidence map, either independently or in combination. Applied pressure or force is computed on a patch, or portion, of an ultrasound image. For example, a portion of the image is computed in any pixel size (e.g., a portion that is w pixels by w pixels), and each patch returns a scalar value. Scalar values from N-patches are concatenated to generate a ND feature vector. Mapping between the tangent space of the ND feature vector and the Cartesian space is provided using the image Jacobian $J_I$. Using the image Jacobian, the desired constraint to be implemented is a small rate of change of the ND feature vector, written as equation 8:

$$|J_I J_k \Delta q|_n \le \epsilon_I \quad \text{(Eq. 8)}$$

where n=1, 2. For example, an L1 norm squared computes each patch independently and does not allow any patch to deviate beyond the specified tolerance. In another example, an L2 norm squared treats each patch with equal weight. The feature vector is be scaled by a diagonal matrix W, with diagonal elements representing the relative importance of each patch, as expressed in equation 9:

$$|W J_I J_k \Delta q|_n \le \epsilon_I \quad \text{(Eq. 9)}$$

Figure 4:
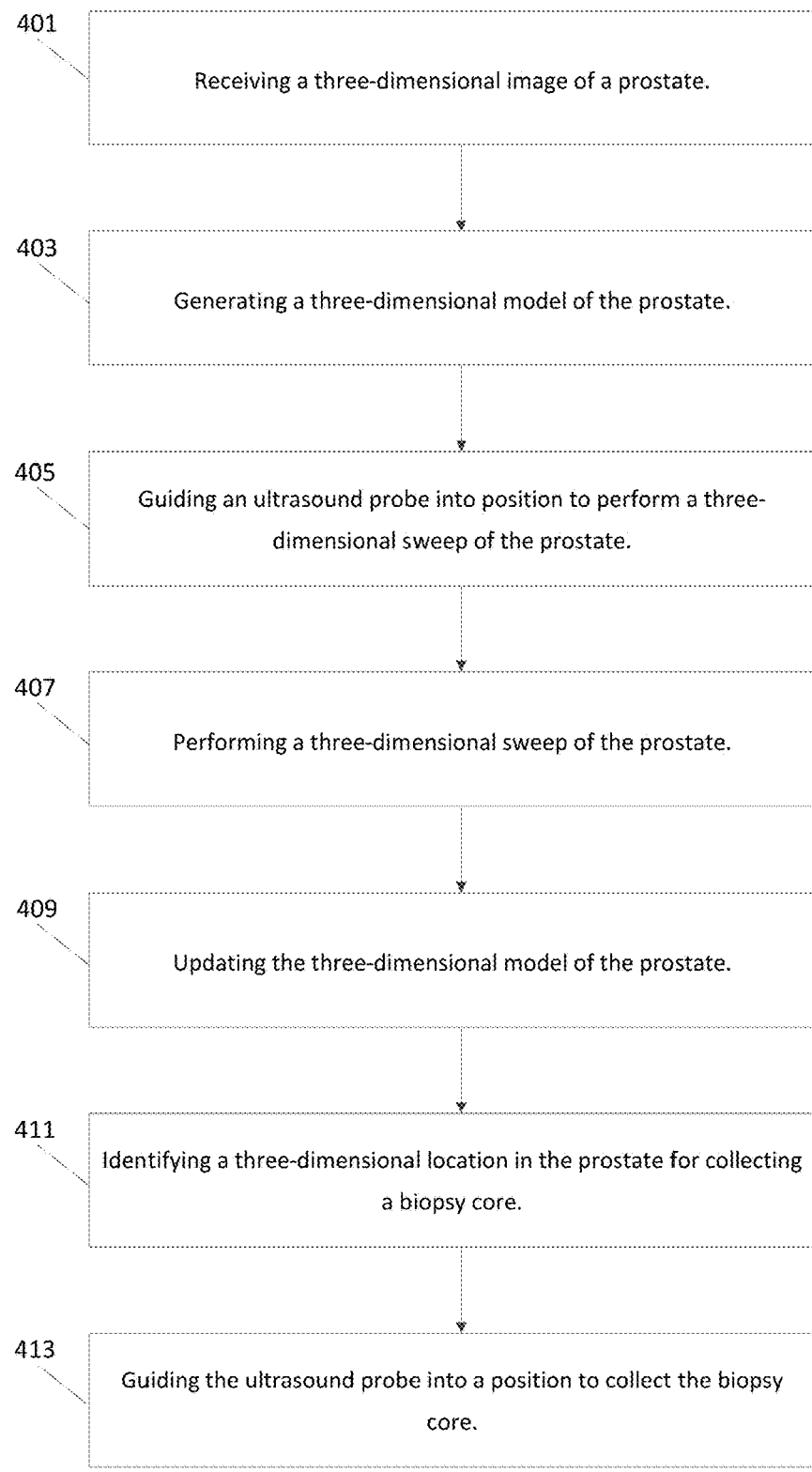
FIG. 4 illustrates a flowchart of an embodiment of a method for ultrasound guided prostate needle biopsies using a robotic arm.

FIG. 4 illustrates a flowchart of an embodiment of a method for ultrasound guided prostate needle biopsies using a robotic arm. The method is implemented by the system of FIG. 1 and/or a different system. A processor, such as a processor of an imaging system, performs acts 401, 403, 405, 409, 411, and 413. The imaging system, using a probe guided by the processor, performs act 407. A user may assist or perform acts 405 and/or 413.

Additional, different or fewer acts may be provided. For example, acts 409-413 are not performed. As another example, act 409 is not provided. In yet another example, acts 401-409 are not provided. In other examples, acts for configuring for imaging, calibrating, activating and/or imaging are provided.

The method is provided in the order shown. Other orders may be provided, and acts may be repeated.

At act 401, a three-dimensional image of a prostate is received, such as a preoperative MRI image. The three-dimensional image is received from a three-dimensional imaging system prior to the ultrasound procedure. Alternatively, a three-dimensional image of the prostate may be captured initially by scanning the patient in another act.

The data is received by scanning. Alternatively, the data is received by loading from memory or transfer over a network.

At act 403, a three-dimensional model of the prostate is generated using the three-dimensional image. For example, during preoperative planning, an automatic segmentation is performed on the three-dimensional image data (e.g., MRI map), and a patient specific anatomical model of prostate is generated. Further, the biomechanical properties of the prostate may be determined (i.e., Young's modulus and the Poisson's ratio) using nominal values reported from literature, or the personalized values extracted from elastography scans of the patient are used. Any modeling may be used. The model is a three-dimensional representation of the prostate with or without surrounding tissues. Rather than a purely voxel intensity representation, other information, such as tissue properties, bio-mechanical properties or relationships, scale, orientation, or other information, may be included in the model.

At act 405, the ultrasound probe is guided into a position for a three-dimensional ultrasound sweep of the prostate. For example, the user selects an operating mode for the robotic arm allowing the user to move the ultrasound probe into position for the sweep. In one embodiment, the user selects a freestyle mode that allows the user to move the probe freely, only restricted by the mechanical limits of the robotic arm. Alternatively, or in addition to the freestyle mode, a compliant mode may be selected by the user to allow weightless movement of the ultrasound probe.

At act 407, a three-dimensional ultrasound sweep of the prostate is performed. For example, when the user has localized the prostate, the user manually or automatically acquires a three-dimensional sweep of the prostate. For example, the user selects an operating mode for the robotic arm allowing the user to manually perform the three-dimensional sweep, or enables the system to automatically perform the prostate sweep. In one embodiment, an RCM mode is selected by the user to restrict the motion of the ultrasound probe about a fixed point on the ultrasound probe, such as a distal end or tip of the ultrasound probe. The user then controls movement of the probe as constrained in the RCM mode. Alternatively, an "auto sweep" mode is selected to automatically guide the ultrasound probe through the three-dimensional ultrasound sweep of the prostate. The system tracks the ultrasound images to rotate the probe automatically based on prostate image information. In another example, the system tracks the ultrasound images in RCM mode and/or "auto sweep" mode to maintain consistent and adequate pressure by the ultrasound probe.

Figure 3A:
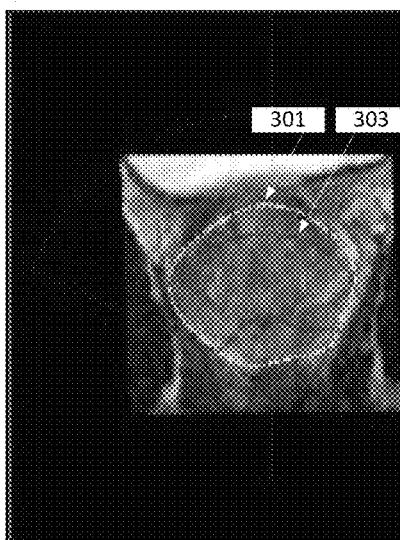
FIGS. 3A-B depict examples of a prostate segmented in an MRI image and an ultrasound image.
Figure 3B:
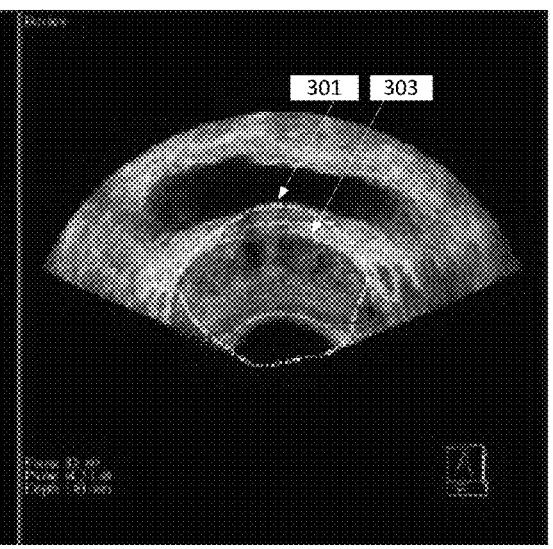

At act 409, the three-dimensional model of the prostate is updated using image data from the three-dimensional ultrasound prostate sweep. For example, the three-dimensional ultrasound image is automatically segmented and an updated three-dimensional model of the prostate is generated based on the ultrasound image. For example, the three-dimensional model is updated to account for prostate deformation caused by the ultrasound probe. Further, feature locations identified using the preoperative MRI are updated in the updated three-dimensional model, accounting for the effects of the prostate deformation by updating feature locations in the three-dimensional model. For example, FIGS. 3A-B depict examples of a prostate segmented in an MRI image and an ultrasound image. FIG. 3A depicts a preoperative MRI image with a prostate outline 301 identified from the MRI image and a prostate outline 303 from a corresponding ultrasound image (i.e., FIG. 3B). FIG. 3B depicts a real-time ultrasound image with the prostate outline 301 identified from the preoperative MRI image (i.e., FIG. 3A) and a prostate outline 303 from the ultrasound image. As such, changes to the three-dimensional model are made to account for the change in shape of the prostate during the ultrasound procedure. In an example, registration between the preoperative MRI data and the real-time ultrasound data is established using the anatomical probe orientation. For example, locations from the three-dimensional preoperative or diagnostic image are mapped with corresponding locations from the three-dimensional ultrasound image. The probe orientation and position is determined, and in combination with the ultrasound scan data, is used to determine the orientation, position, and scale of the ultrasound data relative to the MR data. Further refinement, such as warping, may be used. The updated three-dimensional model is generated using preoperative MRI data and the real-time ultrasound data to determine known feature boundaries and may be enhanced using the nominal or personalized biomechanical properties of the patient.

The three-dimensional image data is fused and provided to the user real-time. An image is generated from both data sets or separate images are generated from the separate data sets. The images show the same anatomy form a same perspective, providing information from both types of imaging. The ultrasound information provides representation in real-time or during the procedure. The MR information may provide greater detail and/or additional information.

At act 411, a three-dimensional location in the prostate is identified as a target for collecting a biopsy core. For example, the location is identified based on the updated three-dimensional model of the prostate. The location and size are determined using the fused information.

At act 413, a needle guide on the ultrasound probe is guided into a position to collect the biopsy core, based on the identified three-dimensional location in the prostate. For example, the user selects an operating mode for the robotic arm. For example, the user selects the RCM mode, restricting movement of the ultrasound probe about the tip of the probe. The user then manually moves the ultrasound probe into position to collect the biopsy core, passively guided by the robotic arm. Thus, based on the three-dimensional model, the user aligns the probe so the biopsy needle guide is in position to target the biopsy core identified in the three-dimensional model. In another example, the user selects an automatic mode where in the robotic arm automatically moves the ultrasound probe into position to collect the biopsy core. In this example, the user marks a target location in the three-dimensional model, and the robotic arm is automatically moved (e.g., following RCM principles) to align the needle guide to the location in the prostate corresponding to the marked location in the three-dimensional model.

When the needle guide is aligned with the desired biopsy core location, the user selects the lock mode. The lock mode maintains the position of ultrasound probe with respect to the target location, and restricts all movement of the ultrasound probe. Acts 411 and 413 are repeated to take multiple biopsy core samples.

Additionally, in one or more embodiments, a calibration act is performed. For example, the robotic arm is calibrated for the handle and tip of the ultrasound probe with respect to coordinate system for the joints of the robotic arm. Further, the system is calibrated for other object coordinates, such as the ultrasound machine itself, the patient table, etc., to be used for collision avoidance constraints. Other calibration may be used to align the preoperative data coordinate system with the robotic or ultrasound coordinate system.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

We claim:

1. A system for ultrasound guided prostate needle biopsies using a robotic arm, the system comprising:
   a processor configured to receive a preoperative three-dimensional image of a prostate, wherein the processor is further configured to generate a three-dimensional model of the prostate based on the received image;
   a multi-link robotic arm comprising:
      a plurality of joints;
      an end-effector attached to one of the plurality of joints;
      an ultrasound probe attached to the end-effector, wherein the ultrasound probe is operably connected to the processor to capture an ultrasound image, wherein the preoperative three-dimensional image was captured using a different imaging modality from the ultrasound image, wherein the processor updates the three-dimensional model of the prostate based on the captured ultrasound image;
      a position sensor for at least one of the plurality of joints, the position sensor operably connected to the processor to map the position of the ultrasound probe with the updated three-dimensional model; and
      a force sensor operably connected to the processor, wherein the force sensor is configured to detect input forces to the end-effector,
   wherein the processor, the position sensor and the force sensor comprise a control loop configured to control manipulation of the ultrasound probe based on updates to the three-dimensional model of the prostate, and
   wherein the robotic arm is configured to operate in a first operating mode restricting movement of the ultrasound probe about a distal end of the ultrasound probe to maintain pressure on the prostate based on consecutively captured ultrasound images in automatic performance of a three-dimensional ultrasound sweep of the prostate.

2. The system of claim 1 wherein the force sensor is attached to a handle of the ultrasound probe.

3. The system of claim 2 wherein the robotic arm is configured to operate in a plurality of other operating modes to restrict movement of the ultrasound probe, the plurality of other operating modes comprising:
   a second operating mode restricting movement of the ultrasound probe by mechanical limits of the robotic arm;
   a third operating mode passively guiding movement of the ultrasound probe into a position to collect a biopsy core;
   a fourth operating mode restricting all movement of the ultrasound probe; and
   a fifth operating mode restricting movement of the ultrasound probe based on analysis of captured ultrasound images.

4. The system of claim 3 wherein the processor is configured to identify the biopsy core based on the received three-dimensional image of the prostate and the captured ultrasound image of the prostate.

5. The system of claim 1 wherein the pressure is maintained on the prostate based on de-correlation between the consecutively captured ultrasound images.

6. The system of claim 1 wherein the pressure is maintained on the prostate based on a difference in a strain on prostate tissue between the consecutively captured ultrasound images.

7. The system of claim 1 wherein the pressure is maintained on the prostate based on an image confidence map generated based on the consecutively captured ultrasound images.

8. The system of claim 1 wherein the pressure is maintained on the prostate based de-correlation between the consecutively captured ultrasound images, strain on prostate tissue between the consecutively captured ultrasound images and an image confidence map generated based on the consecutively captured ultrasound images.

9. The system of claim 1, wherein the control loop is configured to provide adjustable compliance of the multi-link robotic arm.

10. The system of claim 1 wherein the control loop is configured to restrict motion of the ultrasound probe.

11. The system of claim 1 wherein the preoperative three-dimensional model comprises a voxel representation of the prostate with prostate information.

12. The system of claim 11 wherein the prostate information comprises tissue properties, biomechanical properties, or biomechanical relationships.

13. The system of claim 1 wherein the processor is configured to identify a size of a biopsy core based on the received three-dimensional image of the prostate and the captured ultrasound image of the prostate.

* * * * *